United States Patent [19]

Park

[11] 4,179,349
[45] Dec. 18, 1979

[54] PORTABLE PROBE TO MEASURE SENSITIZATION OF STAINLESS STEEL

[75] Inventor: Jang Y. Park, Downers Grove, Ill.

[73] Assignee: The United States of America as represented by the United States Department of Energy, Washington, D.C.

[21] Appl. No.: 945,924

[22] Filed: Sep. 26, 1978

[51] Int. Cl.² ............................................. G01N 27/46
[52] U.S. Cl. ............................ 204/195 R; 204/195 F; 204/195 C
[58] Field of Search ............... 204/1 T, 195 R, 195 C, 204/195 F

[56] References Cited

U.S. PATENT DOCUMENTS

| | | | |
|---|---|---|---|
| 3,077,446 | 2/1963 | Van Den Berg | 204/195 F |
| 3,337,440 | 8/1967 | Nestor | 204/195 C |
| 3,449,232 | 6/1969 | Bailey | 204/195 C |
| 3,466,238 | 9/1969 | Mahieu et al. | 204/195 C |
| 3,684,679 | 8/1972 | Smith et al. | 204/195 C |
| 3,808,105 | 4/1974 | Rozeanu | 204/1 T |
| 4,006,063 | 2/1977 | Ensanian | 204/1 T |

*Primary Examiner*—T. Tung
*Attorney, Agent, or Firm*—R. V. Lupo; Frank H. Jackson; Donald P. Reynolds

[57] ABSTRACT

An electrochemical cell for making field measurements of metals such as stainless steel comprises a cylinder containing a reservoir of an electrolyte, a reference electrode, a capillary tube connecting the electrolyte to the surface of the metal to be measured and another electrode in electrical contact with the electrolyte. External connections from the reference electrode, the other electrode, and the sample to a measuring device provide means for maintaining the potential of the electrolyte while sweeping the potential difference between the electrolyte and the metal. Such a sweep enables the determination of a current-voltage characteristic that is a measure of sensitization in the metal.

4 Claims, 2 Drawing Figures

PORTABLE PROBE TO MEASURE SENSITIZATION OF STAINLESS STEEL

CONTRACTUAL ORIGIN OF THE INVENTION

The invention described herein was made in the course of, or under, a contract with the UNITED STATES DEPARTMENT OF ENERGY.

BACKGROUND OF THE INVENTION

This invention relates to the testing of materials. In particular, this invention comprises an electrochemical cell that is useful for making field measurements of samples of stainless steel to see if the samples have been sensitized.

A problem that is well known to those who work with stainless steel is that of sensitization. Sensitization is a localized loss of the anti-corrosive properties of the stainless steel, either in its manufacture or in fabrication by welding. Stainless steels having chromium concentrations in the range of 18%, such as types 304, 316, and the like, are sensitized when heating to temperatures of 800°–1200° K. causes a formation of the compound chromium carbide in the stainless steel. Both chromium and carbon move within the stainless steel by diffusion, but the carbon moves much faster. Chromium carbide is formed preferentially at grain boundaries, combining with the chromium there to leave localized regions of a mixture with reduced concentrations of free chromium. If the localized regions are reduced to concentrations of the order of 12% or less, the anti-corrosive properties of the stainless steel are affected markedly, and the stainless steel is rendered subject to corrosion and cracking. This is a matter of great concern in stainless steels that are used for piping and the like in nuclear reactors. Sensitization has been observed in some stainless steel pipes that have cracked in service, and sensitization is believed to be the major cause of this cracking. It is desirable to have a non-destructive method of testing 304, 316, or similar high-chromium stainless steels in place to assure that the installed piece has not been sensitized.

It is an object of the present invention to provide an electrochemical cell for field testing of stainless steels for sensitization. Other objects will become apparent in the course of a detailed description of the invention.

SUMMARY OF THE INVENTION

A portable electro-chemical cell comprises a reservoir containing an electrolyte, a standard calomel electrode having a terminal disposed in electrical contact with the electrolyte, a graphite electrode that is also in contact with the electrolyte, and a capillary tube that establishes a capillary connection between the standard calomel electrode and the electrolyte near the surface of a sample to be examined. A comparison of the charge transferred in response to a swept electrical potential difference between the graphite electrode and the test sample provides a measure of properties of the sample. The calomel electrode provides a potential for comparison. The cell is usable in any physical orientation and is portable enough to make useful measurements on installed stainless steels to determine whether a pipe or other structure of stainless steel has been sensitized by welding or other treatment involving heat.

BRIEF DESCRIPTION OF THE DRAWINGS

FIG. 2 is a plot of current-voltage characteristics obtained by the apparatus of the present invention on a typical sample.

DETAILED DESCRIPTION OF THE INVENTION

Figure 1:
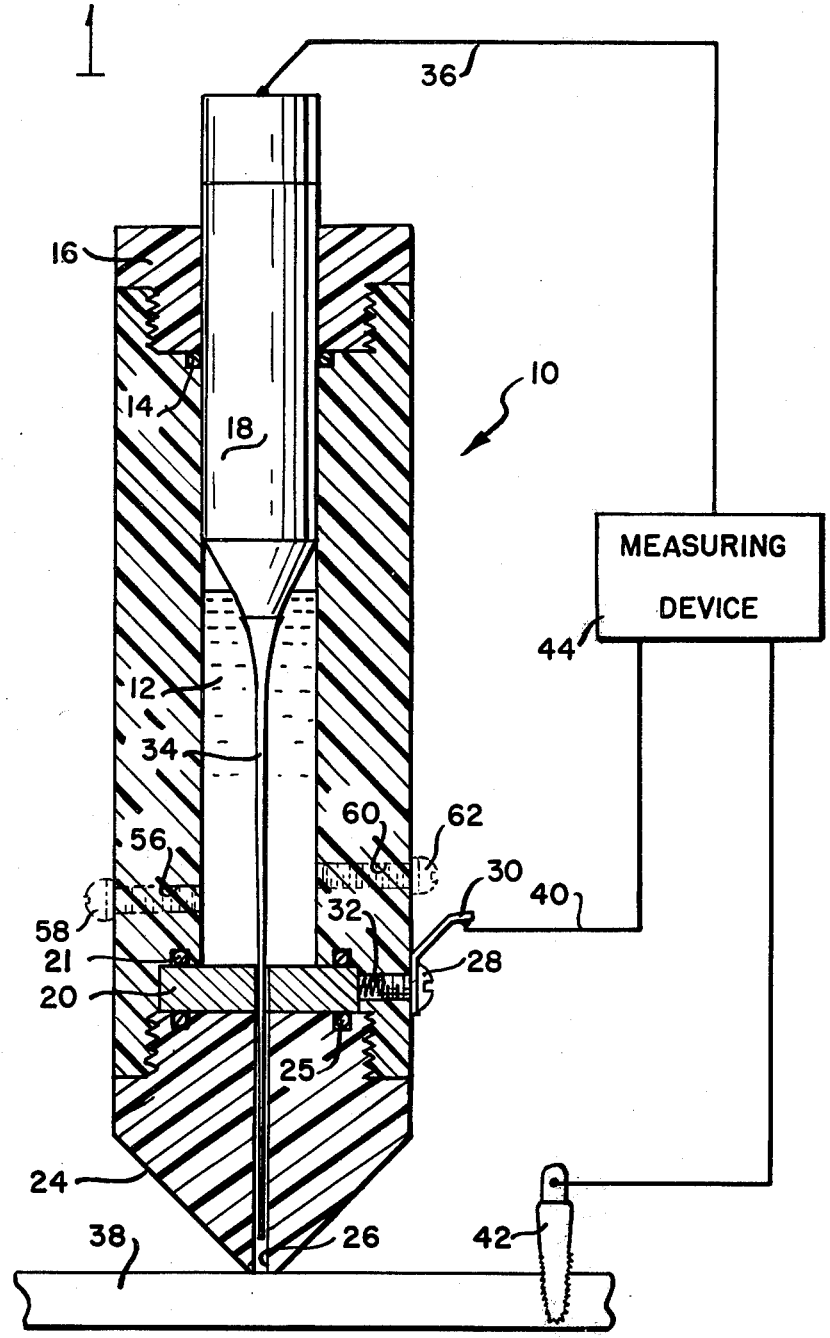
FIG. 1 is an axial cross-sectional view of the cell of the present invention.

FIG. 1 is an axial sectional view of the present invention. In FIG. 1, cylinder 10 is hollowed to contain an electrolyte 12. Cylinder 10 is made of a material that is an electrical insulator and that is inert to the electrolyte. It is convenient, although not necessary, to make cylinder 10 of a transparent organic polymer such as polymethyl methacrylate, sold under trade names that include Lucite and Plexiglas. Cylinder 10 is counterbored and tapped at both ends. Retaining cap 16, also an electrical insulator, is threaded to engage the threads at an end of cylinder 10 and retaining cap 16 also serves to compress an O-ring 14. Retaining cap 16 is hollow to admit electrode 18, a standard calomel electrode that extends into cylinder 10 and electrolyte 12. O-ring 14 forms a seal between the hollow portion of cylinder 10 and electrode 18.

At the other end of cylinder 10 an electrode 20 terminates the hollow portion of cylinder 10 and forms a seal with the hollow portion of cylinder 10 by compressing O-ring 21. Electrode 20 is a circular disk, made preferably of graphite, with a hole in the center. Electrode 20 is compressed against O-ring 21 by capillary tip 24 which is threaded into cylinder 10 at one end and has a conical tip at the other. Capillary tip 24 is made of an electrical insulator like that of cylinder 10 and is transparent in the preferred embodiment. Capillary tip 24 is sealed against leakage by O-ring 25. A capillary tube 26 passes through capillary tip 24 to establish contact through the hole in electrode 20 with electrolyte 12. External electrical contact with electrode 20 is made through cylinder 10 by terminal screw 28 which supports lug 30 and makes electrical contact with spring 32 which is in electrical contact with electrode 20. The calomel electrode 18 has an external wire 36 that connects one end of the electrode for use. The other end of calomel electrode 18 is in electrical contact with electrolyte 12 through capillary tube 34, which extends into capillary tube 26.

The cell of the present invention is shown in FIG. 1 in measuring position near a sample 38 or stainless steel. Capillary tip 24 is placed on sample 38 so that electrolyte 12 makes electrical contact with sample 38 through capillary tube 26. A wire 40 is connected to lug 30, and a mechanical clamp 42 makes electrical contact with the sample 38. Wires 36 and 40 and the clamp 42 are connected electrically to an electronic control device 44 which is a 3-terminal device, a Potentiostat, for monitoring electrical voltage at wire 36 with respect to clamp 42 as a result of applying electrical voltage to wire 40 with respect to clamp 42. The electrical voltage between wire 36 and the clamp 42 and the current through wire 40 and clamp 42 are to be measured. Electrode 18 is operated as a reference standard that is not allowed to draw current.

FIG. 2 is a plot of a current-voltage characteristic obtained on a sample of 304 stainless steel before and after the sample was sensitized by heating. Curve 50 was obtained from the sample as received and curve 52 represents the same sample after it has been sensitized by heating to about 870° K. for a day. Electrolyte 12 was 1 N $H_2SO_4$+0.01 M KSCN in water. For each of the samples the measuring procedure took three steps. First, the specimen was subjected for five minutes to the current flow resulting from a voltage of −500 millivolts applied to the sample 38 with respect to wire 36. The specimen was then passivated by the application for two minutes of a constant voltage of +200 millivolts to the sample 38 with respect to wire 36. The voltage of sample 38 was then decreased linearly at a rate of two millivolts per second, and the current flow from electrode 20 to sample 38 was recorded. The sweep was continued until the current approached zero. Thus, curves 50 and 52 may be considered either as current-voltage plots or, since the voltage was swept as a function of time, the area enclosed within each of the curves 50 and 52 is directly proportional to the amount of charge transfer during this sweep. That charge is visibly larger in curve 52, from the sensitized sample, than the curve of figure 50, obtained from the sample that was not sensitized.

When the electrode of the present invention is used to measure sensitization, the measuring process changes the electrolyte 12 chemically, so that fresh electrolyte 12 must be added before another measurement is made. This may be done by removing either retaining cap 16 or capillary tip 24, pouring out the electrolyte, and replacing it. An alternate embodiment of the invention for changing electrolyte is indicated in dashed lines in FIG. 1, in which first drain hole 56 is drilled through cylinder 10 and is threaded to receive and engage gasketed cap screw 58. A fill hole 60 is similarly sealed with a gasketed cap screw 62. Both gasketed cap screws 58 and 62 are preferably non-metallic to avoid interference with the measurement of sensitization. It may also be desirable to add electrolyte by dropper or syringe at the tip of capillary tube 26 to insure contact between the sample and electrolyte 12 regardless of the orientation of the cell.

The embodiments of the invention in which an exclusive property or privilege is claimed are defined as follows:

1. A probe for field measurement of sensitization of a test piece of stainless steel at a test point comprising:
   a reservoir containing an electrolyte;
   a connecting capillary tube connecting the reservoir to the test piece;
   a standard calomel reference electrode having an extended capillary tube disposed in the connecting tube and open near the test point, and further having an external connecting wire;
   a graphite electrode disposed in the reservoir in electrical contact with the electrolyte;
   an external electrical connection disposed outside the reservoir;
   means for connecting the external electrical connection to the graphite electrode; and
   means for establishing electrical contact with the test piece near the test point.

2. The probe of claim 1 wherein the electrolyte is 1 N $H_2SO_4$+0.01 M KSCN in water.

3. The probe of claim 1 comprising in addition means for removing and replacing the electrolyte.

4. A portable probe for use in any orientation to measure sensitization of a test piece of stainless steel at a test point comprising:
   a cylinder of an electrically insulating plastic;
   a standard calomel electrode having a capillary tip, the standard calomel electrode disposed in the cylinder;
   an end cap threaded to an end of the cylinder and forming a seal with the cylinder and the standard calomel electrode;
   a disc-shaped graphite electrode disposed near a second end of the cylinder, the graphite electrode having an aperture to admit the capillary tip of the standard calomel electrode, the graphite electrode forming with the cylinder and the end cap a reservoir;
   an electrolyte disposed in the reservoir;
   a capillary tip having a substantially conical exterior, the capillary tip threaded to the second end of the cylinder and supporting the disc-shaped graphite electrode, the capillary tip having a capillary tube that connects with the aperture of the disc-shaped graphite electrode and admits the capillary tip of the standard calomel electrode;
   an external lug connected electrically to the disc-shaped graphite electrode; and
   a clamp connected electrically to the test piece,
   whereby application of an electrical voltage according to a predetermined scheme between the external lug and the clamp and measurement of electric current flow at the external lug provide a measure of sensitization of the test piece.

* * * * *